(12) United States Patent
Hirsiger et al.

(10) Patent No.: US 7,147,624 B2
(45) Date of Patent: Dec. 12, 2006

(54) NEEDLE PROTECTING DEVICE

(75) Inventors: Michel Hirsiger, Kirchberg (CH); Daniel Scheidegger, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 181 days.

(21) Appl. No.: 10/384,397

(22) Filed: Mar. 7, 2003

(65) Prior Publication Data

US 2003/0168366 A1     Sep. 11, 2003

Related U.S. Application Data

(63) Continuation of application No. PCT/CH01/00467, filed on Jul. 31, 2001.

(30) Foreign Application Priority Data

Sep. 8, 2000     (DE) ................. 100 44 383

(51) Int. Cl.
*A61M 5/32*     (2006.01)

(52) U.S. Cl. ...................... 604/198; 604/192

(58) Field of Classification Search ............... 604/198, 604/195, 192, 197, 263, 187, 163, 110, 264; 206/365, 438; 220/8

See application file for complete search history.

(56) References Cited

U.S. PATENT DOCUMENTS

| | | | | |
|---|---|---|---|---|
| 4,897,083 A | * | 1/1990 | Martell | 604/192 |
| 5,336,199 A | * | 8/1994 | Castillo et al. | 604/198 |
| 5,593,387 A | | 1/1997 | Rupp | |
| 5,772,636 A | * | 6/1998 | Brimhall et al. | 604/198 |
| 5,795,336 A | * | 8/1998 | Romano et al. | 604/192 |
| 6,080,135 A | * | 6/2000 | Van Stokkum | 604/198 |

* cited by examiner

*Primary Examiner*—Nicholas D. Lucchesi
*Assistant Examiner*—Matthew F. DeSanto
(74) *Attorney, Agent, or Firm*—Dorsey & Whitney LLP (57) ABSTRACT

A needle protecting device including a carrier and a needle cover connected to the carrier at a distal needle cover end, the needle cover including a proximal needle cover end which is movable relative to the distal needle cover end such that the needle cover may be elongated along the length of the needle from an exposing position in which the injection needle protrudes through the needle cover to a protecting position in which the needle cover surrounds the injection needle at least as far as its tip, wherein the needle cover is elongated by an elasticity force, and wherein locking elements, including at least a distal locking element and a proximal locking element, lock the needle cover against shortening in its protecting position.

23 Claims, 5 Drawing Sheets

NEEDLE PROTECTING DEVICE

CROSS-REFERENCE TO RELATED APPLICATIONS

This application is a continuation of International Patent Application No. PCT/CH01/00467, filed on Jul. 31, 2001, which claims priority to German Patent Application No. 100 44 383.4, filed on Sep. 8, 2000, the contents of which are both incorporated herein by reference.

BACKGROUND

The invention relates to a needle protecting device for an apparatus for administering an injectable product or for sampling a body fluid. In one embodiment, the apparatus is preferably an injection apparatus, in particular an injection pen. The needle protecting device protects a user against injuries from an injection needle and protects the injection needle from damaging handling. In addition, the needle protecting device can advantageously also prevent the injection needle, which can be of any gauge or size, from being seen, and in such a development thus forms a blind.

An injection syringe comprising a protruding injection needle and a flexible needle protecting device is known from WO 96/11026. When the injection needle is injected into a tissue, the needle protecting device is compressed in the longitudinal direction, i.e., along the longitudinal axis, of the injection needle and thus shortened, in order to expose the injection needle. The needle protecting device is made of a compressible, elastic material and in some embodiments exhibits the form of a bellows. With respect to the injection needle, this needle protecting device exclusively provides a blind, but no protection against handling and injuries, since for compressing the needle protecting device, only the elasticity force of the elastic needle protecting device itself ever has to be overcome.

SUMMARY

It is an object of the invention to provide a needle protecting device which is flexible with respect to its length and nonetheless protectively surrounds an injection needle after use, for example after an injection, such that unintentional handling of the injection needle is prevented.

The invention relates to a needle protecting device for an administering or sampling apparatus comprising an injection needle. The needle protecting device comprises a carrier, a needle cover and a means for generating an elasticity force acting on the needle cover. The needle cover is elongated by the elasticity force in the longitudinal direction of the injection needle, from an exposing position in which the injection needle protrudes through it to a protecting position in which it surrounds the injection needle up to the tip of the needle. The carrier may be connected to the administering or sampling apparatus.

In one preferred embodiment, the needle protecting device may be handled separately from such an apparatus and in particular may be handled independently. In principle, in some embodiments, however, the carrier can also be an integrated component of an administering or sampling apparatus and in particular can be formed by the casing of the apparatus. The injection needle is preferably fixed to the carrier which, in this embodiment, thus also forms a needle carrier. In this embodiment, the injection needle is fixed such that the connection between the carrier and the apparatus simultaneously also forms a fluid connection between the injection needle and a reservoir of the apparatus. The carrier can, however, also serve only as a carrier for the needle protecting device and be slid over the injection needle, which in this case already protrudes from the apparatus, and fixed to the apparatus, such that a defined positional relationship arises between the injection needle and the needle protecting device. In both cases, once the carrier has been fixed to the apparatus, the injection needle proximally protrudes beyond the carrier. The needle cover comprises a distal end and a proximal end. The distal end is connected to the carrier. The proximal end is movable relative to the distal end. In this sense, the needle cover is flexible in the longitudinal direction of the injection needle. It exhibits its largest length in the protecting position, and surrounds the injection needle at least up to the tip of a needle and preferably slightly beyond the tip of the needle. The needle cover preferably hides the injection needle, i.e., it preferably forms a needle blind, though this is not absolutely necessary.

In accordance with the invention, the needle cover in its protecting position is mechanically locked against being shortened. The lock is formed by locking elements which are connected to each other and may be moved with respect to the longitudinal direction of the injection needle as far as a locking position. In the locking position, the locking elements support the needle cover situated in the protecting position on the carrier and thus prevent the needle cover from being shortened. In one embodiment, each of the locking elements are preferably locked to each other in pairs, one locking element of the pair against the other locking element of the pair, such that relative movement between the locking elements in the longitudinal direction of the injection needle is no longer possible in the locking position. Two locking elements are in principle sufficient for locking the needle cover, namely a distal locking element in the locking position and a proximal locking element in the locking position. In some embodiments, any suitable lock or locking structures can be used, including suitable complementary locking structures.

In one embodiment, until the locking position is reached, the proximal locking element is movable relative to the distal locking element such that a locking means formed by the locking elements is elongated together with the needle cover. The distal locking element is immovably fixed to the carrier in the longitudinal direction of the injection needle, at least in the protecting position of the needle cover, in order to form the support for the locking means relative to the carrier. The proximal locking element is immovably connected to the proximal end of the needle cover in the longitudinal direction of the injection needle. The locking elements together can form the needle cover alone. In this case, the proximal locking element also simultaneously forms the proximal end of the needle cover.

In one embodiment, the distal locking element is preferably connected to the carrier completely rigidly. The carrier and the distal locking element can be made as one piece, for example as a single plastic injection-molded part. In principle, however, the distal locking element can also be movably connected to the carrier, as one or more pieces, for example folding about an axis perpendicular to the longitudinal axis of the injection needle, including if the size of the needle is 31 G or a higher gauge number. However, a folding movement would have to be prevented or at least made substantially more difficult in the locking position of the locking elements.

In one embodiment, the elasticity force can be generated pneumatically. Preferably, however, in other embodiments it is generated by a mechanical spring member which, in the exposing position of the needle cover, is biased towards the tip of the needle in the longitudinal direction or along the length of the needle.

In some preferred embodiments, the needle cover is itself a spring member which is biased in exposing position. The needle cover is formed as bellows which are elastic in the longitudinal direction of the injection needle. The bellows can be made of an elastomeric material, and in this embodiment can generate the elasticity force solely through its inherent material elasticity. Instead, or in combination with the embodiment made of an elastomeric material, an additional spring element, for example a spiral spring pressure-biased in the exposing position, can generate the elasticity force. Even in those cases in which the elasticity force of the needle cover is formed only by inherent qualities of the cover or an integrated spring element, such a needle cover may be thought of as a spring member in the sense of the invention.

In embodiments in which a needle cover is not formed by the locking elements, but is provided in addition to the locking elements, such a needle cover can already surround the injection needle at least up to or preferably beyond the tip of the needle, including if the size of the needle is 31 G or a higher gauge number, in an initial position in which it is not yet locked, and in this way can form a blind even before an injection or infusion. In this embodiment, such a needle cover may be particularly preferably formed as a spring member, as already described.

In the exposing position, the locking elements are preferably fixed to the carrier in the longitudinal direction or, in other words, along the longitudinal axis, of the injection needle by means of a releasable connection, in order to prevent the locking elements from being inadvertently moved into the locking position. The connection can be a non-destructively releasable latching connection between the carrier and the proximal locking element.

In some embodiments, the elasticity force can permanently act on the locking elements, preferably on the proximal locking element. In this case, the locking elements are prevented from moving into the locking position by the releasable connection to the carrier. In this case, the releasable connection may preferably be formed such that it is released by an external, active or positive operation. This active operation can advantageously be performed by the needle cover as the needle is injected, if for example the needle cover already serves as a blind in a non-locked, initial position, as described above. In such an embodiment, the needle cover is compressed as the injection needle is injected, thereby releasing the connection between the locking elements and the carrier. In one preferred embodiment of such a needle cover as a spring member, the needle cover is shortened as far as the proximal locking element and connected to the proximal locking element in the exposing position thus reached. If the injection needle is removed from the tissue again, thus relieving the needle cover again, the needle cover is elastically elongated again, thereby slaving the proximal locking element.

In some embodiments, a stopper acting in the longitudinal direction of the injection needle is preferably formed on the carrier, said stopper being abutted by a needle cover which may be shortened from a non-locked initial position. The stopper defines the maximum length by which the injection needle protrudes beyond the needle cover in the exposing position. The stopper thus defines the maximum depth of penetration of the injection needle. In some preferred embodiments, the position of the stopper or of a counter stopper connected to the needle cover can be varied with respect to the longitudinal axis of the injection needle, thereby adjusting the maximum depth of penetration of the needle. The depth of penetration may preferably be varied by exchanging an element forming the counter stopper. An assortment of needle protecting devices can very easily be formed with identical needle covers, but with different counter stoppers. The Applicant reserves the right to also direct a claim to this, without the locking means.

In some preferred embodiments, the present invention comprises locking means comprising not only a distal locking element and a proximal locking element which is movable relative to the distal locking element, but also other movable locking elements. Preferably, each of the locking elements are locked to each other in pairs, movable with respect to each other in pairs and locked against each other in pairs in the locking position of the locking means, such that relative movement in the longitudinal direction of the injection needle is no longer possible.

In some embodiments, the locking elements can be connected to each other, for example by folding, such that they are folded onto each other in the exposing position and unfolded in the locking position and locked in this unfolded position. In one preferred embodiment, the locking elements are guided on each other, linearly shifting, in the longitudinal direction of the injection needle. In one preferred embodiment, they form a telescope comprising at least one shifting telescopic piece formed by the proximal locking element. In some embodiments, a telescope is formed comprising a number of locking elements, shifting in the longitudinal direction of the injection needle relative to the carrier, as movable telescopic pieces. A locking telescope formed in this way is and can be adapted to be very stable against lateral forces. The locking telescope is particularly stable if the telescopic pieces, i.e., the locking elements, are formed by cylindrical sleeves. In this case, the locking elements are particularly stably guided relative to and/or on each other in the longitudinal direction of or along the injection needle.

In some embodiments, the movable locking element or number of movable locking elements are preferably prevented from moving out of the locking position by each two adjacent locking elements latching with each other in the locking position. In some embodiments, the latching connection formed between each pair of adjacent locking elements is releasable only by destroying one of the latching means forming the latching connection.

In one embodiment, a preferred latching connection between two locking elements is formed by a catch and a catch stopper acting in the longitudinal direction of the injection needle. The catch projects radially inwardly or outwardly from one of the locking elements and is elastically bendable. In the event of a relative movement of the locking elements of the respective pair, the catch slides along the catch stopper with which it forms the latching connection in the locking position, and is thereby elastically bent. When or shortly before the locking position is reached, the catch is released from its catch stopper and moves into its relieved position. The position of the catch and the catch stopper in the locking position is such that the latching connection is not automatically released when the locking element moves back, but only by destroying or deliberately bending back the catch using an external force. In some embodiments, preferably at least two such latching connections are formed between each two adjacent locking elements in the locking position, which makes it more difficult to release the locking position inadvertently or with destructive intent.

If the carrier is formed from a plastic material or a number of plastic materials as an injection-molded part, the carrier and the locking elements can be injected-molded as one piece. The movable locking element or number of moving locking elements can be connected to each other and to the carrier via break-off points. Equally, however, the carrier and each movable locking element can each be individually made as a plastic injection-molded part and subsequently assembled.

BRIEF DESCRIPTION OF THE DRAWINGS

One exemplary preferred embodiment of the invention will now be described in conjunction with the accompanying figures.

DETAILED DESCRIPTION

Figure 1:
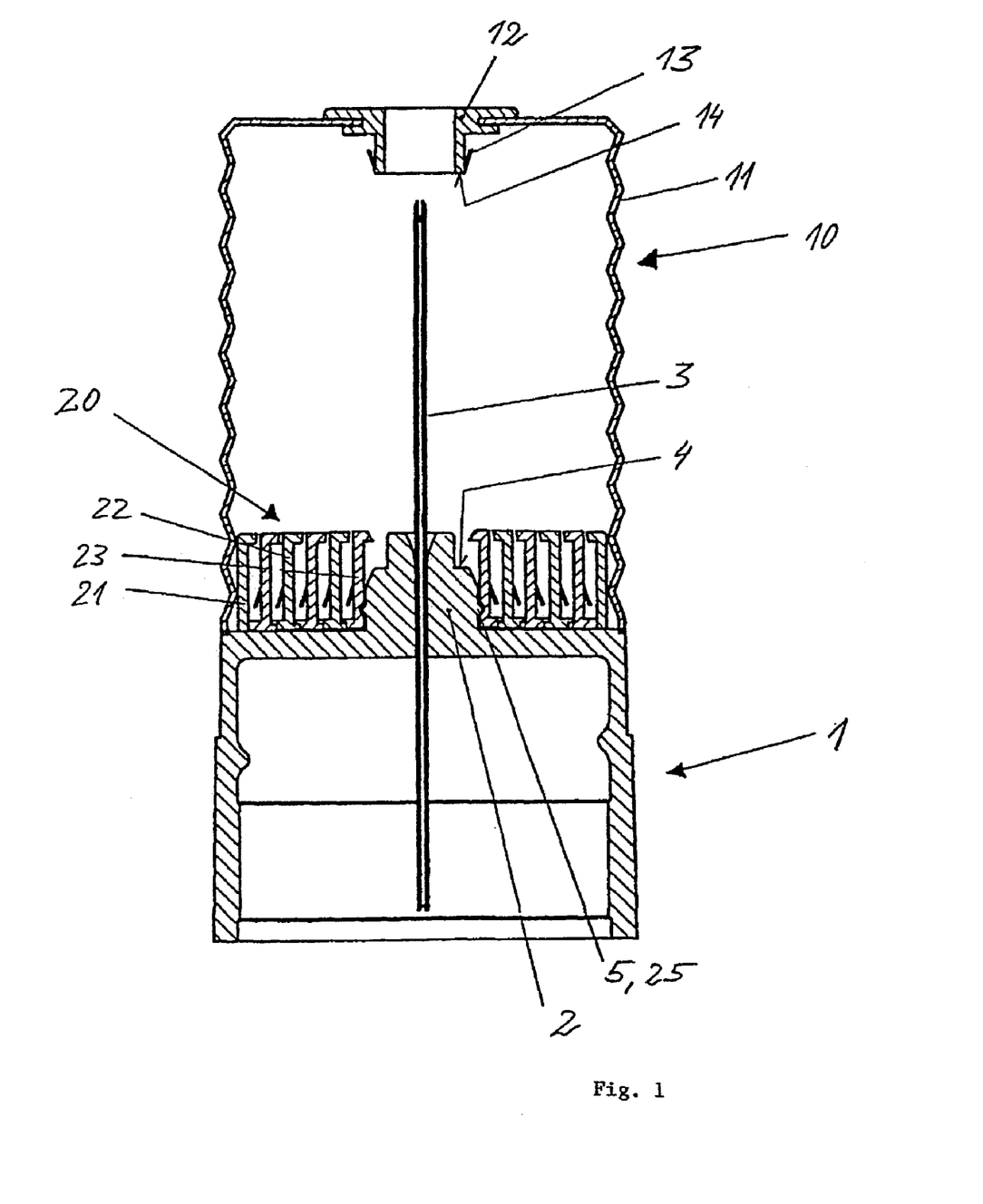
FIG. 1 depicts one embodiment of a needle protecting device in accordance with the present invention in an initial position.
Figure 2:
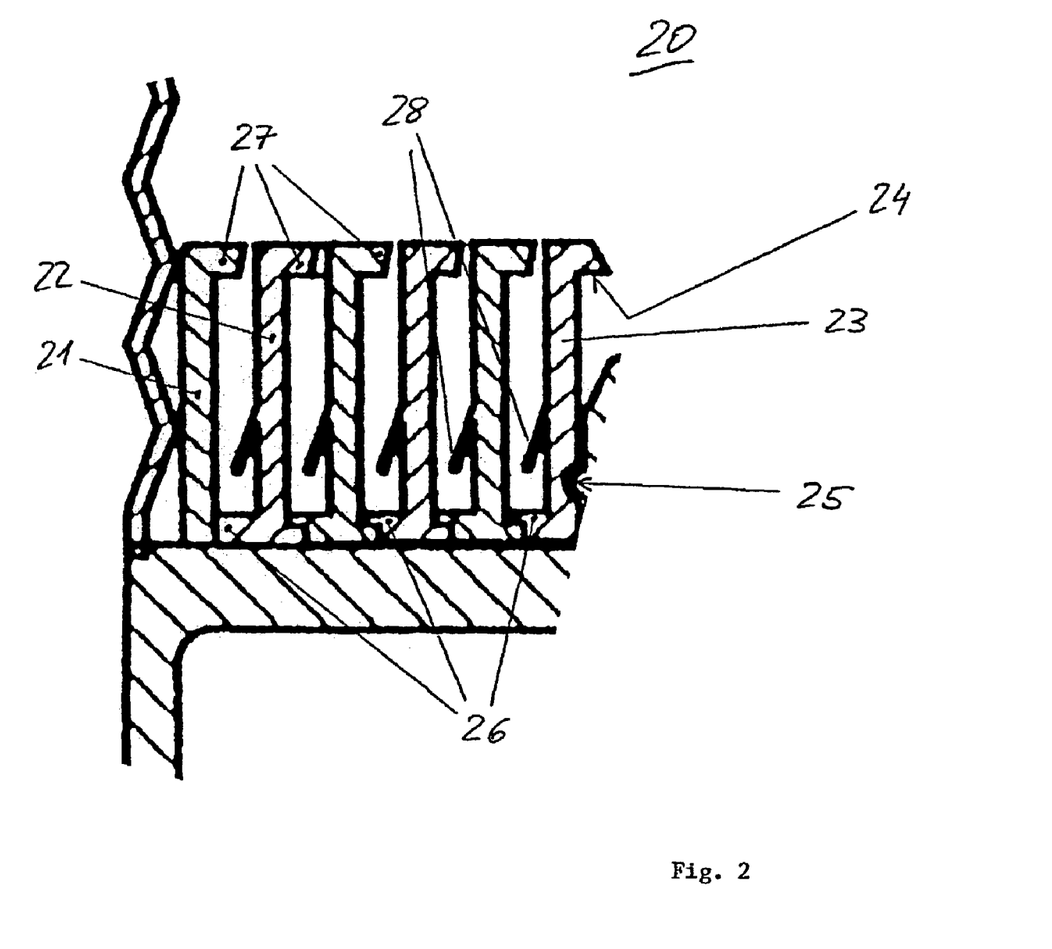
FIG. 2 depicts one embodiment of a locking means of the needle protecting device.

FIG. 1 shows a longitudinal section of a needle protecting device comprising a needle cover 10 which is attached to a needle carrier 1 and may be locked in a protecting position by means of a locking means 20. In a detail of FIG. 1, FIG. 2 shows the locking means 20.

FIG. 1 shows the needle protecting device in an initial position, before an injection needle 3 is injected into a tissue, for example beneath the human skin. It should be appreciated that the needle protecting device of the present invention may be used with or adapted for use with any size injection needle, including 31 G needles or needles of a higher or lower gauge number. In the initial position, the needle cover 10 surrounds the injection needle 3 beyond the tip of the needle. In the initial position, the needle cover 10 prevents the injection needle 3 from being seen, i.e. in the initial position, the needle cover 10 forms a needle blind. The needle cover 10 can be shortened in the longitudinal direction of the injection needle 3, out of the initial position, such that the injection needle 3 protrudes through the needle cover 10.

The needle carrier 1 is formed by a sleeve body comprising a base on a proximal sleeve carrier end. The sleeve body is provided with a single-flight screw thread on its inner surface, in order to be able to screw the needle carrier 1 onto a casing of an administering or sampling apparatus. Instead of by means of a screw connection, the connection to the apparatus could also be established by any suitable connective, attaching or locking structure, for example, by a bayonet lock, friction fitting, etc., or simply by plugging it on and preferably latching it. In a central region of the needle carrier 1, a cylindrical body 2 projects from the needle carrier base towards the tip of the needle, i.e. in the proximal direction. A bore which is centered with respect to the needle holder 1 leads through the cylindrical body 2, the injection needle 3 protruding through said bore and being fixed in said bore in the longitudinal direction. When the connection between the needle holder 1 and the administering or sampling apparatus is established, a distal end of the injection needle 3 is pushed through a septum which seals an opening of a reservoir for an injectable product, in particular a medical fluid, or of a receptacle in a known way.

The needle cover 10 comprises bellows 11 and a functional body 12 which fulfils the function of a stopper and a slaving means, as is described below. The bellows 11 surround the injection needle 3, on all sides and is elongated radially inwards at a proximal end towards the longitudinal axis of the injection needle 3. In the center of the radially elongated region, the functional body 12 is fixed to the bellows. The bellows 12 comprise a passage which is flush with the injection needle 3 and through which the injection needle 3 protrudes beyond the needle cover 10 when it is injected. The passage may be open or unobstructed, or it may be removeably, releaseably or penetrably sealed or blocked by a suitable seal, for example, a membrane of material penetrable by the needle. The bellows 11 are fixedly connected to the needle carrier 1 at its distal end. The proximal end of the bellows 11 and therefore the functional body 12 is freely carried by the bellows 11 and can be shortened toward the needle carrier 1 against an elastic force generated by material elasticity and shaping, when the bellows 11 are compressed.

Figure 3:
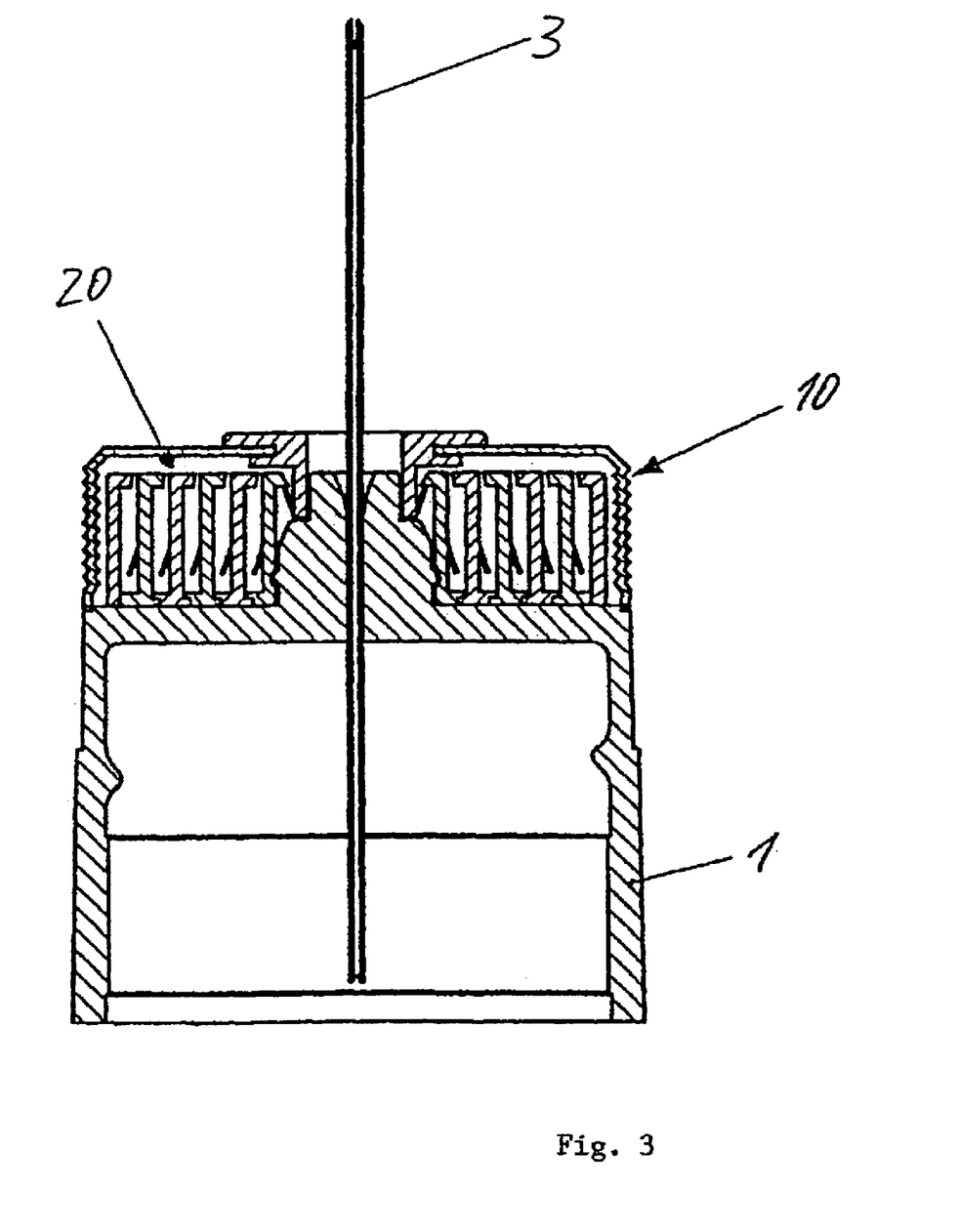
FIG. 3 depicts the needle protecting device in an exposing position.

The bellows 11 can be shortened as far as an exposing position shown in FIG. 3. In the exposing position, the injection needle 3 protrudes through the passage in the functional body 12, beyond the needle cover 10. The maximum length by which the injection needle protrudes beyond the proximal end of the needle cover 10 is defined by a stopper 4 on the needle carrier 1 and a counter stopper 14 formed by the functional body 12. The stopper 4 is formed on the cylindrical body 2, preferably as an annular facing area extending concentrically around the injection needle 3. The counter stopper 14 is formed by a distal counter facing area arranged in alignment on the functional body 12, preferably also an annular area.

Forming the counter stopper 14 for establishing the maximum protruding length of the injection needle 3 and therefore the maximum depth of penetration, on a functional body 12 which may be separately manufactured enables the maximum depth of penetration to be varied in a simple way, namely by manufacturing functional bodies 12 of different lengths. In order to pre-set a desired maximum depth of penetration, the corresponding functional body 12 merely is connected to the bellows 11. Using functional bodies 12 of different lengths, the slight distance exhibited between the stopper 4 and the counter stopper 14 in the initial position of the needle protecting device can be varied in this way.

The locking means 20 comprises a number of locking elements. An outermost locking element is indicated by 21, an innermost locking element by 23, and other locking elements arranged radially in between by 22. The locking elements 21, 22 and 23 are formed by coaxially arranged sleeve bodies of equal length. In the initial position, all the locking elements 21 to 23 are situated in distal positions. In these distal positions, they push against the plane base of the needle carrier 1 facing them.

Figure 4:
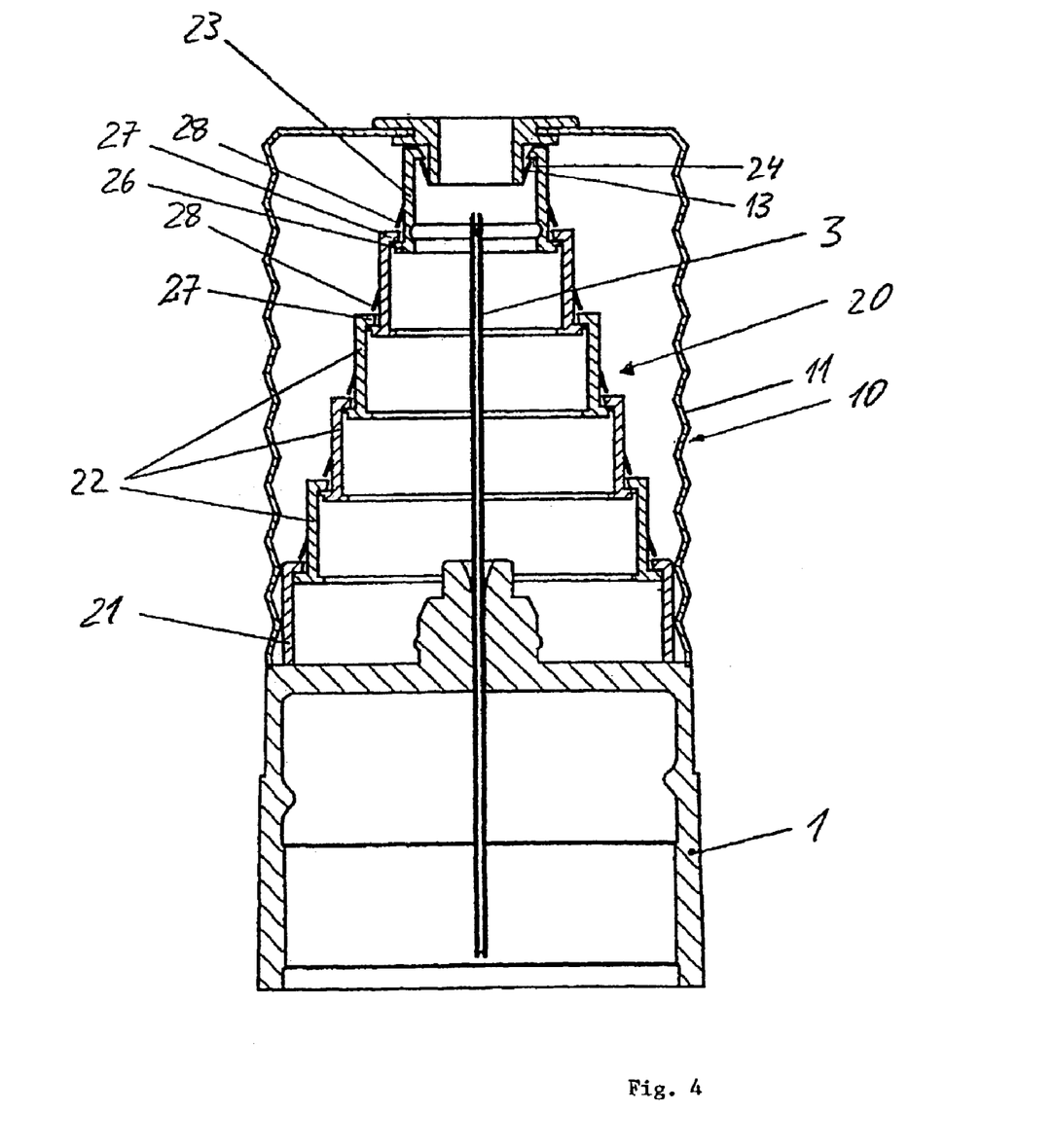
FIG. 4 depicts the needle protecting device in a protecting and locking position.

The locking elements 21 to 23 form a locking telescope which, when extended, as shown in FIG. 4, assumes a locking position. Once the locking position has been reached, the locking elements cannot be shifted back toward their initial position. Due to their positions in the locking position, the outermost locking element will be referred to as the distal locking element 21 and the innermost locking element as the proximal locking element 23.

In the initial position shown in FIGS. 1 and 2, the locking elements 21 are fixed to the needle carrier 1 with respect to the longitudinal axis of the injection needle 3 by means of a latching connection. The latching connection is formed between the cylindrical body 2 and the proximal locking element 23. The latching means of the latching connection are one or more projections radially projecting from the cylindrical body 2 or a circumferential bulge 5 and one or more recesses or a circumferential annular groove 25 on the inner surface of the proximal locking element 23. In the completely retracted state of the locking elements 21 to 23, i.e., in the initial position and in the exposing position, a releasable latching connection is established when the latching means 5 is accommodated in the latching means 25.

The proximal locking element 23 and the locking elements 22 each comprise a collar 26, projecting radially outwardly and preferably, in some embodiments, formed as an annular collar, in their distal foot regions. The other locking elements 22 arranged between the distal locking element 21 and the proximal locking element 23 furthermore each comprise in their foot regions a collar, preferably an annular collar, projecting radially inwardly. In the completely retracted position, the collar 26, projecting radially outwardly, of each of the radially inwardly adjacent locking elements comes to rest over each of the collars projecting radially inwardly. The collars 26, projecting radially outwardly, form clamps for the collars projecting radially inwardly. Proceeding from the proximal locking element 23, which is fixed to the needle carrier 1 with respect to the longitudinal direction of the injection needle 3 by means of the latching connection 5, 25, each of the locking elements 22 movable with respect to the needle carrier 1 is fixed by its neighboring element arranged radially further inwardly. The distal locking element 21 is fixedly connected to the needle holder 1, for example manufactured in one piece.

Each of the locking elements 21 to 23 comprises a collar 27, projecting radially inwardly and also preferably being formed as an annular collar, at a proximal end. The collars 26 in the foot regions and at the distal ends, respectively, and the collars 27 at the proximal end of the locking elements 21 to 23 delimit the extended movement of the locking telescope, by forming pairs of stoppers and counter stoppers.

At least one catch 28 is formed on each of the locking element 23 and the other movable locking elements 22. The at least one catch 28 projects radially outwards from the outer surface of each of the locking elements 22 and 23. Preferably, a number of the catches 28 are arranged on a level, equally distributed over the outer surface of each of the locking elements 22 and 23.

Each of the catches 28 is formed as a clip or tongue which projects from the outer surface of the respective locking element in a direction pointing toward the distal end of the locking element. Each of the catches 28 comprises a free distal end. The catches 28 are elastically bendable toward the outer surface of the locking element on which they are formed.

In addition to the stopper function already described, the functional body 12 also fulfils the function of a slaving means for the locking means 20. If the bellows 11 is compressed and therefore shortened until the stopper 4 and the counter stopper 14 push against each other, a latching connection is automatically established between the functional body 12 and the proximal locking element 23. On the side of the proximal locking element 23, the collar 27—preferably, in one embodiment, an annular collar—projecting radially inwardly at the proximal end of the locking element 23 acts as a latching means. On the side of the functional body 12, a catch 13 acts as a latching means of this latching connection. In the exemplary embodiment, a preferred embodiment, a number of catches 13 are provided equally distributed on an outer surface of the functional body 12, preferably directly behind the counter stopper 14. The catches 13 correspond to the catches 28 on the locking elements 22 and 23. However, each catch 13 points in a proximal direction, i.e. it points forwards from the outer surface of the functional body 12. In some embodiments, the collar 27 of the proximal locking element 23, which, via a distal facing area, forms a catch stopper 24 for each of the catches 13, is preferably flared radially outwardly on its surface area, in order to aid the catch 13 in sliding off smoothly.

In the following, the functionality of the needle protecting device before, during and after the injection needle 3 is injected is described, by referring to FIGS. 1 to 4.

For injecting, the needle cover 10 (shown in FIG. 1 in its initial position) is placed on the injection point via its proximal end, in particular the functional body 12, such that the injection needle 3 is pointing to the injection point with its needle tip. The administering or sampling apparatus is then pressed against the injection point. By compressing the bellows 11, the injection needle 3 slides through the passage in the functional body 12 and penetrates into the tissue. The maximum depth of penetration is reached when the stopper 4 and the counter stopper 14 push against each other.

As the bellows 11 are shortened, the catch 13 or number of catches 13 engage with the collar 27 (projecting inwardly) of the proximal locking element 23. The catch or catches 13 thereby slide over the surface area of the collar and are thus elastically bent radially inwardly, such that the needle cover 10 can be shortened further. Directly before the two stoppers 4 and 14 push against each other, ideally at the same time as they push against each other, the catch 13 or number of catches 13 are released from the protruding collar or collars 27 of the proximal locking element 23 and snap back forward, elastically and radially outwardly, behind the collar or collars 27 of the proximal locking element 23. Due to this restoring movement, each catch 13 abuts the catch stopper 24 formed by the collar 27. The needle cover 10 and the proximal locking element 23 are then hooked to each other with respect to the longitudinal direction of the injection needle 3 by the latching connection 13, 24. In some embodiments, this latching connection cannot be non-destructively released.

The exposing position then assumed, in which the needle carrier 1 and the needle cover 10 are abutting and the needle cover 10 and the locking means 20 are latched to each other, is shown in FIG. 3. In the exposing position, the product is administered by way of injection or infusion.

In the exposing position, though also beforehand in the initial position, the locking means 20 is very short in the longitudinal direction of the injection needle 3 due to its multi-member design comprising a number of locking elements 21 to 23 movable relative to each other. In this position, it merely requires a cylindrical storage space with a diameter which is smaller than the diameter of the needle carrier 1 and also smaller than the diameter of the needle cover 10. The length of the storage space corresponds to the length of the longest of the locking elements 21 to 23; in the exemplary embodiment, the locking elements 21 to 23 are of equal length. In one embodiment, the locking elements 21 to 23 are formed by cylindrical, preferably circular cylindrical, sleeves which surround each other and are arranged coaxially about the longitudinal axis of the injection needle 3. In principle, a locking telescope could also be formed by non-sleeve-shaped locking elements, for example by linearly shifting tongues guided on each other. Such a locking means is also regarded as a locking telescope in the sense of the invention. Forming the locking telescope using sleeve bodies which when relatively shifted are linearly guided on each other via cylindrical surface areas results in a particularly stabile arrangement during relative shifting and, in particular, in the extended locking position.

Once administering the product has been concluded, the injection needle 3 is removed again from the tissue. As it is removed, the needle cover 10, i.e., the bellows 11, are relieved of pressure and elongated into the protecting position shown in FIG. 4 as a result of their own elastic restoring force. In the protecting position, the needle cover 10 surrounds the injection needle 3 up to and beyond the tip of the needle. The protecting position is identical to the initial position with respect to the shape and/or position of the needle cover 10. In the protecting position, however, the needle cover 10 is locked against shortening again by the locking means 20.

Since the needle cover 10 is latched or hooked to the locking means 20 when the exposing position is reached, elastically elongating the needle cover 10 initially slaves the proximal locking element 23 as the needle cover 10 is elongated. The proximal locking element 23 slides off, in the longitudinal direction of the injection needle 3 on the inner surface of the nearest locking element 22 in the radially outward direction, until its stopper collar 26 abuts the counter stopper formed by the collar 27 of the adjacent locking element 22, projecting radially inwardly. Because of the catch forces to be overcome, a number of the movable locking elements 22 and 23 will advance in the proximal direction, before the stoppers 26 and 27 abut each other in their respective pairs. During the relative movements of the movable locking elements 22 and 23, the catches 28 are elastically bent radially inwardly as they slide along the respective collars 27. Once the collars 28 have arrived proximally in front of the collars 27, respectively cooperating with them, the catches 28 snap back forwards, radially outwardly, due to their own elastic restoring force, and together with the collars 27 then form the stopper and counter stopper with respect to the locking elements 22 and 23 shifting along the longitudinal axis of the injection needle 3 in the distal direction. The stopper position at 27, 28 is reached shortly before or at the same time as the stoppers 26 and 27 abut each other. The elasticity force of the bellows 11 is sufficiently large to shift all the movable locking elements 22 and 23 into their individual locking positions with respect to the adjacent locking element. The needle cover 10 can only be moved out of the protecting position by destroying the retracting lock. In the protecting position, and if it is sufficiently stable and/or strong, the needle cover 10 protects against handling and injury. If the locking elements 21 to 23 are formed cylindrically, the locking means 20 can instead also protect against handling and injury. Advantageously, double protection is realized.

Figure 5:
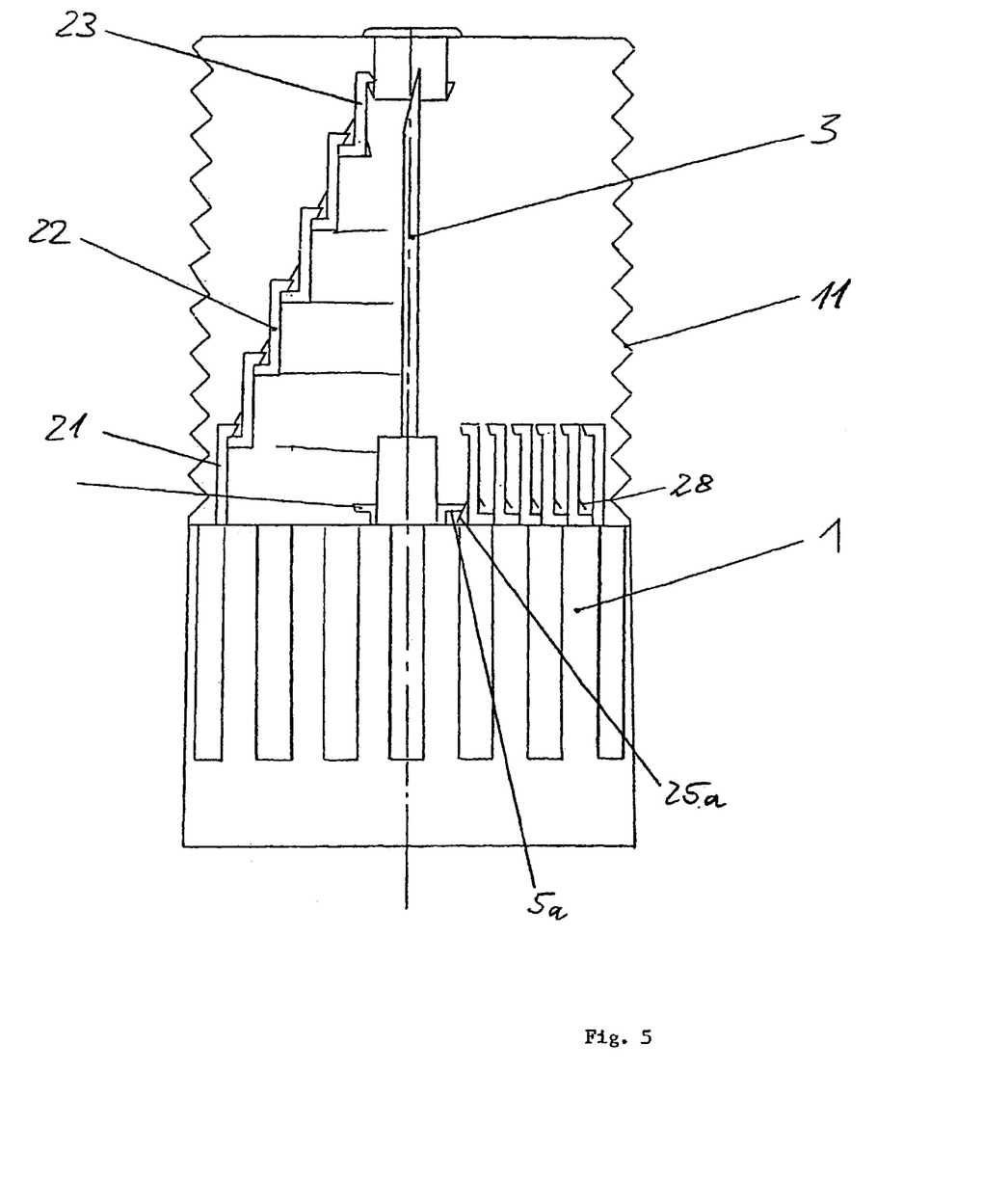
FIG. 5 depicts the needle protecting device of the present invention, further comprising a modified latching connection between the locking means and a carrier.

FIG. 5 shows a needle protecting device which only differs from the needle protecting device in FIGS. 1 to 4 with respect to the latching connection which exists between the locking means 20 and the needle holder 1 in the initial position and the exposing position. The latching connection of the embodiment of FIG. 5 is formed by a catch 25a and a catch counter stopper 5a in the manner of the retracting lock 27, 28 before locking.

In the foregoing description, embodiments of the invention, including preferred embodiments, have been presented for the purpose of illustration and description. It is not intended to be exhaustive or to limit the invention to the precise form or forms disclosed. Obvious modifications or variations are possible in light of the above teachings. The embodiment is chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle protecting device for an apparatus for administering an injectable product or for sampling a body fluid, wherein the administering or sampling is performed by means of an injection needle, said needle protecting device comprising:
   a) a carrier connected to or integrated with said administering or sampling apparatus;
   b) a needle cover connected to said carrier at a distal needle cover end, wherein the distal needle cover end abuts the carrier, and the needle cover comprising a proximal needle cover end movable relative to said distal needle cover end such that the needle cover may be elongated in the longitudinal direction of said injection needle from an exposing position in which the injection needle protrudes through the needle cover to a protecting position in which the needle cover substantially surrounds the injection needle at least as far as a tip of the needle, wherein the needle cover produces and is elongated by an elasticity force, said needle cover comprising a catch at an interior portion of the proximal needle cover end; and
   c) locking elements inside the needle cover, comprising at least a distal locking element and a proximal locking element, for locking the needle cover against shortening in said protecting position, said locking elements movably connected to each other and are in a locked position with respect to the needle when the needle cover catch engages with said proximal locking element and said needle cover is elongated, said distal locking element locked on the carrier at least in the locked position, wherein the distal locking element abuts the carrier, and the proximal locking element is immovably connected to the catch at the interior portion of the proximal needle cover end.

2. The needle protecting device as set forth in claim 1, wherein said elasticity force is generated by a spring member which is biased in the exposing position of the needle cover.

3. The needle protecting device as set forth in claim 2, wherein the needle cover forms the spring member.

4. The needle protecting device as set forth in claim 1, wherein the locking elements are guided on each other, linearly shifting, in the longitudinal direction of the injection needle.

5. The needle protecting device as set forth in 4, wherein the locking elements form a telescope comprising at least one telescopic piece which may be shifted relative to the carrier.

6. The needle protecting device as set forth in claim 1, wherein the needle cover comprises an elastic bellows.

7. The needle protecting device as set forth in claim 1, wherein the needle cover is not locked in an initial position in which it surrounds the injection needle at least as far as the tip of the needle, and may be shortened against the elasticity force out of said initial position into said exposing position.

8. The needle protecting device as set forth in claim 1, wherein a spring member which generates the elasticity force comprises a portion forming the catch, wherein the catch engages with the proximal locking element when the injection needle is injected into a tissue.

9. The needle protecting device as set forth in claim 1, wherein locking elements which are movable relative to the carrier are fixed on the carrier with respect to the longitudinal direction of the injection needle by means of a releasable connection between the proximal locking element and the carrier.

10. The needle protecting device as set forth in claim 1, wherein the distal locking element is rigidly connected to the carrier.

11. The needle protecting device as set forth in claim 1, wherein the size of the needle is no more than 31 G.

12. A needle protecting device comprising a carrier and a needle cover connected to the carrier at a distal needle cover end, wherein the distal needle cover end abuts the carrier, the needle cover including a proximal needle cover end which is movable relative to the distal needle cover end such that the needle cover may be moved along the length of the needle from an exposing position in which the injection needle protrudes through the needle cover to a protecting position in which the needle cover generally surrounds the injection needle, wherein the needle cover produces an elasticity force, and a plurality of locking elements, wherein the locking elements are inside the needle cover, wherein one of the plurality of locking elements engages a catch located at an interior portion of the proximal needle cover end, and wherein another of the plurality of locking elements abuts the carrier such that said locking elements lock the needle cover against moving in its protecting position.

13. The needle protecting device as set forth in claim 12, said locking elements comprising at least a distal locking element and a proximal locking element.

14. The needle protecting device as set forth in claim 13, the locking elements moveably connected to each other and moveable along the length of the needle into a locked position when the needle cover is moved into its protecting position, the distal locking element locked on the carrier at least in a locked position.

15. The needle protecting device as set forth in claim 14, wherein the proximal locking element is immovably connected to the proximal needle cover end.

16. The needle protecting device as set forth in claim 14, wherein the proximal locking element forms the proximal needle cover end.

17. A needle protecting device for an apparatus for administering an injectable product or for sampling a body fluid, wherein the administering or sampling is performed by means of an injection needle, said needle protecting device comprising:
 a carrier connected to or integrated with said administering or sampling apparatus;
 a needle cover connected to said carrier at a distal needle cover end, wherein the distal needle cover end abuts the carrier, and the needle cover comprising a proximal needle cover end movable relative to said distal needle cover end such that the needle cover may be elongated in the longitudinal direction of said injection needle from an exposing position in which the injection needle protrudes through the needle cover to a protecting position in which the needle cover substantially surrounds the injection needle at least as far as a tip of the needle, wherein the needle cover produces and is elongated by an elasticity force, and wherein the needle cover is not locked in an initial position in which it surrounds the injection needle at least as far as the tip of the needle, and may be shortened against the elasticity force out of said initial position into said exposing position, said needle cover comprising a catch at an interior portion of the proximal needle cover end; and
 locking elements, comprising at least a distal locking element and a proximal locking element, inside the needle cover for locking the needle cover against shortening in said protecting position, said locking elements movably connected to each other and in a locked position with respect to the needle when the needle cover catch engages with said proximal locking element and said needle cover is elongated, said distal locking element locked on the carrier at least in the locked position, wherein the distal locking element abuts the carrier, and said proximal locking element immovably connected to the catch at the interior portion of the proximal needle cover end.

18. The needle protecting device as set forth in claim 17, the locking elements moveably connected to each other and moveable along the length of the needle into a locked position when the needle cover is moved into its protecting position, the distal locking element locked on the carrier at least in a locked position.

19. The needle protecting device as set forth in claim 18, wherein the proximal locking element is immovably connected to the proximal needle cover end.

20. The needle protecting device as set forth in claim 18, wherein the proximal locking element forms the proximal needle cover end.

21. A needle protecting device for an apparatus for administering an injectable product or for sampling a body fluid, wherein the administering or sampling is performed by means of an injection needle, the needle protecting device comprising:
 a) a carrier connected to or integrated with the administering or sampling apparatus;
 b) a needle cover connected to the carrier at a distal needle cover end, wherein the distal needle cover end directly abuts the carrier, and the needle cover comprising a proximal needle cover end movable relative to the distal needle cover end such that the needle cover may be elongated in the longitudinal direction of the injection needle from an exposing position in which the injection needle protrudes through the needle cover to a protecting position in which the needle cover substantially surrounds the injection needle at least as far as a tip of the needle, wherein the needle cover produces and is elongated by an elasticity force; and
 c) locking elements surrounded by the needle cover and movably connected to each other, comprising at least a distal locking element and a proximal locking element for locking the needle cover against shortening in said protecting position, the distal locking element locked to and directly abutting the carrier, the locking elements in a locked position when both the needle cover is in the protecting position and the proximal locking element is immovably connected to the proximal needle cover end.

22. A needle protecting device comprising a carrier and a needle cover connected to the carrier at a distal needle cover end, wherein the distal needle cover end has a surface in direct contact with the carrier, the needle cover including a proximal needle cover end which is movable relative to the distal needle cover end such that the needle cover may be moved along the length of the needle from an exposing position in which the injection needle protrudes through the needle cover to a protecting position in which the needle cover generally surrounds the injection needle, wherein the needle cover produces and is moved by an elasticity force, and wherein a plurality of locking elements are generally inside the needle cover and movably connected to each other lock the needle cover against moving in its protecting position, one of the plurality of locking elements having a surface in direct contact with the carrier, said one of the plurality of locking elements locked to the carrier.

23. A needle protecting device for an apparatus for administering an injectable product or for sampling a body fluid, wherein the administering or sampling is performed by means of an injection needle, said needle protecting device comprising:

a carrier connected to or integrated with said administering or sampling apparatus;

a needle cover connected to said carrier at a distal needle cover end, wherein the distal needle cover end is operably coupled to the carrier, and the needle cover comprising a proximal needle cover end movable relative to said distal needle cover end such that the needle cover may be elongated in the longitudinal direction of said injection needle from an exposing position in which the injection needle protrudes through the needle cover to a protecting position in which the needle cover substantially surrounds the injection needle at least as far as a tip of the needle, wherein the needle cover produces and is elongated by an elasticity force, and wherein the needle cover is not locked in an initial position in which it surrounds the injection needle at least as far as the tip of the needle, and may be shortened against the elasticity force out of said initial position into said exposing position; and locking elements inside the needle cover and movably connected to each other, comprising at least a distal locking element and a proximal locking element for locking the needle cover against shortening in said protecting position, the distal locking element operably coupled to the carrier, the locking elements in a locked position when both the needle cover is in the protecting position and the proximal locking element is immovably connected to the proximal needle cover end.

* * * * *